United States Patent [19]

Grasselli et al.

[11] 4,246,190
[45] Jan. 20, 1981

[54] AMMOXIDATION WITH TELLURIUM CATALYSTS

[75] Inventors: Robert K. Grasselli, Chagrin Falls; Arthur F. Miller, Cleveland; Dev D. Suresh, Warrensville Heights, all of Ohio

[73] Assignee: The Standard Oil Company, Cleveland, Ohio

[21] Appl. No.: 768,252

[22] Filed: Feb. 14, 1977

Related U.S. Application Data

[63] Continuation of Ser. No. 293,795, Oct. 2, 1972, abandoned.

[51] Int. Cl.³ .......................................... C07C 120/14
[52] U.S. Cl. ................................................. 260/465.3
[58] Field of Search ..................................... 260/465.3

[56] References Cited

U.S. PATENT DOCUMENTS

| | | | |
|---|---|---|---|
| 3,625,867 | 12/1971 | Yoshino et al. | 260/465.3 X |
| 3,641,102 | 2/1972 | Reulet et al. | 260/465.3 |
| 3,642,930 | 2/1972 | Grasselli et al. | 260/465.3 X |
| 3,686,265 | 8/1972 | Reulet et al. | 260/465.3 |
| 3,716,496 | 2/1973 | Yoshino et al. | 260/465.3 X |
| 3,741,910 | 6/1973 | Shiraishi et al. | 260/465.3 X |
| 3,746,656 | 7/1973 | Shiraishi et al. | 260/465.3 X |

Primary Examiner—J. P. Brust
Attorney, Agent, or Firm—John E. Miller, Jr.; Herbert D. Knudsen; Larry W. Evans

[57] ABSTRACT

Tellurium catalysts containing at least iron, tellurium and molybdenum plus one of nickel, cobalt or magnesium have been discovered to be especially useful for ammoxidation reactions.

7 Claims, No Drawings

AMMOXIDATION WITH TELLURIUM CATALYSTS

This application is a continuation of our co-pending application Ser. No. 293,795, now abandoned filed on Oct. 2, 1972.

BACKGROUND OF THE INVENTION

Many ammoxidation catalysts are known. Among these known catalysts is a catalyst containing FeTe and Mo as shown by U.S. Pat. No. 3,641,102. Also known are catalysts containing CoMoTe and P, see Canadian Pat. No. 892,632.

The present invention improves these catalysts by the addition of essential elements which significantly enhance the desirability of the catalysts in ammoxidation reactions.

SUMMARY OF THE INVENTION

It has now been discovered by the present invention that catalysts of the formula:

$$A_a B_b C_c Fe_d Te_f D_g Mo_h O_x$$

wherein A is an alkali metal, Tl, In, Cu, Ag or mixture thereof,

B is Ni, Co, Mg or mixtures thereof,

C is W, Cr, Ce, Zn, Cd, Mn, Cu, Ba or mixtures thereof,

D is P, As, Sb, B or mixture thereof, and wherein a and g are independently 0 to about 3, b is about 0.2 to about 12, c is 0 to about 4, d is about 0.1 to about 8, f is about 0.04 to about 4, h is about 6 to about 18, x is the number of oxygens sufficient to satisfy the valence requirements of the other elements present, and where $b > d$, have very desirable activity in ammoxidation reactions. For example, in an ammoxidation of propylene, the per pass conversion has been demonstrated to be significantly higher than the art catalyst with a significant reduction in the ammonia that is unreacted. The higher per pass conversion, of course, is important because more product is obtained, and the lower ammonia breakthrough reduces the ammonium sulfate pollution caused by the neutralization of the ammonia with sulfuric acid.

The important and critical aspect of the present invention is the catalyst. The catalyst may be any catalyst delimited by the general formula above. The fundamental point of the invention is the discovery that the addition of Ni, Co, Mg or a mixture thereof to a FeTeMo catalyst, substantially improves the yields in reactions with these catalysts. Also, it has been discovered that these base catalysts of the invention are improved by the addition of certain optional elements. These optional elements are designated in the formula as those elements where the lower case subscript can be equal to zero. There can be a large number of optical elements in the formula.

With respect to the components of the catalyst, preferred catalysts contain either nickel or cobalt in addition to the base catalyst of FeTeMo. Even more preferred are catalysts that contain nickel and cobalt, for these catalysts have been found to demonstrate superior activity.

With respect to the optional elements, preferred catalysts contain an alkali metal, Tl, In or a mixture thereof. Thus, in the formula A is an alkali metal, Tl, In or a mixture thereof and a is not equal to zero. These catalysts have demonstrated high per pass conversions.

Also with respect to the optional components, catalysts containing chromium, tungsten or cerium have been found to be very desirable. This is especially true with chromium for an example where the optional promoter chromium was used gave the highest per pass conversion of any example run, see Example 13. In the formula, this inclusion of additional elements is accomplished by setting C equal to Cr, W or Ce and making c equal to a number other than zero.

A third set of optional components includes those of P, As, Sb and B. The most common of these components in ammoxidation catalysts is phosphorus. Yet others included in the group have been found to be desirable. Specifically, in the present invention, the inclusion of P and Sb have been found to be especially advantageous. Thus, preferred catalysts contain at least some P or Sb. This is accomplished in the formula by setting D equal to P or Sb and g equal to a number other than zero.

The general formula of the present invention is sufficient to describe to one of ordinary skill in the art how to make the catalysts. These catalysts are made by techniques which are essentially the same as those techniques described in the art for other oxidation catalysts.

Even though there are numerous preparations that may be utilized to give acceptable catalysts, some of the preferred methods of making the catalysts are described in this general discussion and the best methods of preparing the catalysts discovered in the invention are described in the Specific Embodiments.

Normally the catalysts are prepared in the supported form. Thus, in any such preparation the incorporation of the support into the preparation is essential. Preferred supports are the hydrous oxide gels, preferably silica and alumina. Other support materials, such as zirconia, titania, alundum, silicon carbide, alumina-silica, and inorganic phosphates, silicates, aluminates, borates and carbonates are also suitable.

In the preferred preparations the catalysts are prepared from the metal nitrates, halides or oxides. When the nitrates are employed, the nitrate catalyst precursors are denitrified to give the desired oxide catalyst. In the broad concept of the invention, the catalysts can be prepared from any mixture of compounds that can be oxidized to give the desired oxide catalyst.

One preferred method of preparing the catalyst is the co-gelling of the catalyst components in the presence of a hydrous oxide gel. The compounds to be used to make the catalysts are mixed with the supporting gel until a gellation occurs. The gelled mass is dried and calcined.

Another preferred method of preparing large quantities is the spray drying of a slurry of the co-gelled catalyst precursors described above. For normal laboratory preparations, however, the catalysts are most conveniently prepared by co-gelling or co-precipitating the catalyst precursors in an aqueous medium.

An important aspect of the catalyst preparation is the heat treatment given to the catalysts or catalyst precursors after the combination of the various ingredients of the catalyst. No general rule can be given for the optimum heat treatment for a particular catalyst because different catalysts do not react the same way toward heat treatment. Thus, an optimum heat treatment for one catalyst may give an undesirable catalyst when applied to a different composition.

Even though no general rule has been devised for the heat treatment of all catalyst composition, broad temperature parameters appear to apply generally. Temperatures of about 400° C. to about 1000° C. are normally employed in the heat treatments, with temperatures of about 450° C. to about 700° C. being preferred. Temperatures in excess of 1100° C. have been found to be undesirable. Within these guidelines, then, it is a simple task for one of ordinary skill to determine the best heat treatment to be given any particular catalyst within the scope of the present invention.

When used in ammoxidation reactions, the catalysts of the present invention are normally placed in a reactor and brought to reaction temperature in a stream of air. The reaction is then begun by the initiation of the reactant flow.

The preparation of acrylonitrile, methacrylonitrile or mixtures thereof by using the catalysts of the present invention is of special importance. In these reactions, the process is conducted within the limits of the parameters shown by the art. For example, the reactant ratios, the reaction conditions and feed rates are essentially the same as the art reactions. The only difference is that the catalyst of the present invention is employed.

Briefly, the broad conditions under which the ammoxidation of olefins is carried out are as follows. The temperature of the reaction is between about 300° and about 600° C. The reaction may be conducted under subatmospheric, superatmospheric or atmospheric pressure. The reactant ratios based on olefin:ammonia:air range from about 1:0.7 to 1.5:8 to 15. Of course, other forms of molecular oxygen can be employed. The contact time may vary widely, but it is usually under 20 seconds. The reaction can be conducted in either a fixed or fluid bed reactor.

Accordingly, it is readily apparent that the broad limits stated in the art are acceptable for the ammoxidation of olefins using the catalysts of the present invention. Of course, it cannot be stated that the optimum reactor configuration, reactant ratios, conditions and feed rates are optimum for use in the present invention because use of a different catalyst normally alters these features of the process. Yet, it is clear that the optimum operating ranges fall within the limits described and the best embodiments of the invention known are described in the Specific Embodiments.

SPECIFIC EMBODIMENTS

Comparative Example A and Examples 1-12—Comparison of catalysts of the invention to the catalyst of the art in the ammoxidation of propylene.

In parallel experiments, catalysts representing the art and catalysts representing the invention were prepared and tested to determine the activity in the ammoxidation of propylene. The catalysts were prepared as follows:

Comparative Example A $Fe_{10}TeMo_{12}O_x$ 31.8 grams of $(NH_4)_6Mo_7O_{24}.4H_2O$ were dissolved in water and the solution was placed on a hot plate with stirring. To the solution was added 25.2 grams of 40% silica sol sold by Nalco Chemical Company. Stirring and heating was continued for 15 minutes, then 60.6 grams of $Fe(NO_3)_3.9H_2O$ dissolved in water was added and 2.4 grams $TeO_2$ slurried with water was added. The mixture was heated until it began to thicken, then the mixture was transferred to a drying oven and dried at 120° C. for 48 hours. The catalyst was heat treated for five hours at 290° C., three hours at 430° C. and 17 hours at 550° C.

EXAMPLE 1

$Ni_7Fe_3Te_{0.5}Mo_{12}O_x$

In the same manner shown for the catalyst preparation above, 31.8 grams of $(NH_4)_6Mo_7O_{24}.4H_2O$ was dissolved in water and heated on a hot plate with stirring. To this solution, 25.0 grams of 40% silica sol was added and then 30.5 grams of $Ni(NO_3)_2.6H_2O$ dissolved in water. After 15 minutes of heating and stirring 18.2 grams of $Fe(NO_3)_3.9H_2O$ dissolved in water and 1.2 grams $TeO_2$ slurried in water were added. The mixture was heated until it began to thicken. The mixture was then dried in an oven at 120° C. for 40 hours and heat treated at 290° C. for five hours, 430° C. for four hours and 550° C. for 16 hours.

EXAMPLE 2

$Co_7Fe_3TeMo_{12}O_x$

In the same manner as described above, molybdenum and silica sol were added. To this mixture was added a solution of 30.5 grams of $Co(NO_3)_2.6H_2O$ and the mixture was stirred for 15 minutes. To this mixture was added an aqueous solution of 18.2 grams of $Fe(NO_3)_3.9H_2O$ and 2.4 grams of $TeO_2$. The catalyst was dried and heat treated as shown in the preparation of the catalyst for Example 1.

EXAMPLE 3

$Mg_7Fe_3TeMo_{12}O_x$

In the same manner as shown above, a slurry of molybdenum and 22.5 grams of 40% silica was prepared and heated. To this slurry was added 26.9 grams of $Mg(NO_3)_2.6H_2O$ and the slurry was heated for 15 minutes. Then iron and tellurium were added in the same amounts and manner and the catalyst was recovered and heat treated as shown in Example 1.

EXAMPLE 4

$Mg_{2.5}Co_{4.5}Fe_3TeP_{0.5}Mo_{12}O_x$

Following the same procedure as Example 1, the catalyst was prepared by adding aqueous solutions or slurries of the following materials 31.8 grams $(NH_4)_6Mo_7O_{24}.4H_2O$, 0.9 grams $H_3PO_4$, (85%) 24.9 grams 40% silica sol and 19.7 grams $Co(NO_3)_2.6H_2O$. The mixture was heated for 15 minutes, then aqueous solutions or slurries of 9.6 grams $Mg(NO_3)_2.6H_2O$, 18.2 grams $Fe(NO_3)_3.9H_2O$ and 2.4 grams $TeO_2$ were added. The catalyst was recovered and heat treated as shown in Example 1.

EXAMPLE 5

$Mg_{2.5}Ni_{4.5}Fe_3TeP_{0.5}Mo_{12}O_x$

In the same manner as shown in Example 4, the catalyst was prepared using 19.6 grams $Ni(NO_3)_2.6H_2O$ instead of the cobalt nitrate.

EXAMPLE 6

$K_{0.1}Ni_2Co_4Fe_4TeP_{0.5}Mo_{12}O_x$

In the same manner as shown in Example 1, a catalyst was prepared from aqueous solutions or slurries of 31.8 grams $(NH_4)_6Mo_7O_{24}\cdot 4H_2O$, 0.9 grams $H_3PO_4$, 25.7 grams 40% silica sol and a solution of 8.7 grams $Ni(NO_3)_2\cdot 6H_2O$ plus 17.5 grams $Co(NO_3)_2\cdot 6H_2O$. This mixture was heated for 15 minutes, and 24.3 grams $Fe(NO_3)_3\cdot 9H_2O$, 2.4 grams $TeO_2$ and 0.19 grams KOH were added. The catalyst was recovered and heat treated as shown in Example 1.

EXAMPLE 7

$K_{0.1}Ni_{2.5}Co_{4.5}Fe_3TeP_{0.5}Mo_{12}O_x$

In the same manner as shown in Example 6, the catalyst was prepared using solution or slurries of 63.6 grams $(NH_4)_6Mo_7O_{24}\cdot 4H_2O$, 1.7 grams $H_3PO_4$, 53.6 grams 40% silica sol and a mixture of 21.8 grams $Ni(NO_3)_2\cdot 6H_2O$ and 39.3 grams $Co(NO_3)_2\cdot 6H_2O$. The mixture was heated for 15 minutes, and 36.4 grams $Fe(NO_3)_3\cdot 9H_2O$, 4.8 grams $TeO_2$ and 0.37 grams of KOH was added. The catalyst was recovered and heat treated in the same manner as Example 1, except that heat treatment at 550° C. was conducted for 20 hours rather than 16 hours.

EXAMPLE 8

$K_{0.1}Ni_{2.5}Co_{4.5}Fe_3TeP_{0.5}Mo_{12}O_x$

The catalyst of Example 7 was heat treated for an additional three hours at 650° C.

EXAMPLE 9

$K_{0.1}Ni_3Co_5Fe_2TeP_{0.5}Mo_{12}O_x$

The catalyst was prepared according to Example 6 using different relative amounts of cobalt, nickel and iron.

EXAMPLE 10

$Tl_{0.2}Ni_{2.5}Co_{4.5}Fe_3TeP_{0.5}Mo_{12}O_x$

The catalyst was prepared in essentially the same way as Example 7, except that $TlNO_3$ dissolved in dilute nitric acid and $TeCl_4$ were used in the preparation.

EXAMPLE 11

$In_{0.2}Ni_{2.5}Co_{4.5}Fe_3TeP_{0.5}Mo_{12}O_x$

The catalyst was prepared in the same way as Example 10, except that InCl was used rather than the thallium compound.

EXAMPLE 12

$K_{0.1}Ni_{2.5}Co_{4.5}Fe_3Te_{0.5}Sb_{0.5}P_{0.5}Mo_{12}O_x$

The catalyst was prepared in the same manner as Example 6, except that $Sb_2O_3$ was added after the tellurium.

Each of these catalysts contained 20% $SiO_2$.

After such heat treatment, 5 cc. of the catalyst having a size of 20×35 mesh was placed in a fixed bed reactor. The reactor was brought to a temperature of 400° C. under a stream of air, and a feed of propylene:$NH_3$:air:$H_2O$ of 1:1.1:10:4 was begun. The feed rate gave an apparent contact time of six seconds. The reactor was run for 15 minutes with this feed before product collection was begun. Product was collected for 3 minutes and analyzed by gas-liquid chromatography.

The results are stated as follows:

$$\% \text{ conversion} = \frac{\text{moles of reactant reacted}}{\text{moles of reactant fed}} \times 100$$

$$\% \text{ selectivity} = \frac{\text{moles of product obtained}}{\text{moles of reactant reacted}} \times 100$$

$$\% \text{ per pass conversion} = \frac{\text{moles of product obtained}}{\text{moles of reactant fed}} \times 100$$

The results of experiments with various catalysts of the invention as compared to the FeTeMo catalyst of the art are shown in Table I. The per pass conversions to acrylonitrile are based on the propylene converted. The value of the subscript x in the oxygen is easily calculated by providing enough oxygen to satisfy the valence requirements of the other elements present in their oxidation state at 400° C. in the presence of air.

TABLE I

COMPARISON OF CATALYSTS OF THE INVENTION TO THE CATALYST OF THE ART

| Example | Catalyst - Active Ingredients | % Conversion $NH_3$ | % Conversion Propylene | % Selectivity to AN* | % Per Pass Conv. to AN* |
|---|---|---|---|---|---|
| Comp. A | $Fe_{10}TeMo_{12}O_x$ | 67.6 | 87.3 | 46 | 40.0 |
| 1 | $Ni_7Fe_3Te_{0.5}Mo_{12}O_x$ | 82.4 | 86.8 | 60 | 51.9 |
| 2 | $Co_7Fe_3TeMo_{12}O_x$ | 85.1 | 86.2 | 68 | 59.0 |
| 3 | $Mg_7Fe_3TeMo_{12}O_x$ | 81.1 | 86.3 | 59 | 51.2 |
| 4 | $Mg_{2.5}Co_{4.5}Fe_3TeP_{0.5}Mo_{12}O_x$ | 81.1 | 85.0 | 73 | 62.4 |
| 5 | $Mg_{2.5}Ni_{4.5}Fe_3TeP_{0.5}Mo_{12}O_x$ | 93.2 | 81.2 | 69 | 57.3 |
| 6 | $K_{0.1}Ni_2Co_4Fe_4TeP_{0.5}Mo_{12}O_x$ | 89.2 | 64.1 | 73 | 47.0 |
| 7 | $K_{0.1}Ni_{2.5}Co_{4.5}Fe_3TeP_{0.5}Mo_{12}O_x$ | 90.5 | 77.3 | 80 | 62.0 |
| 8** | " | 86.5 | 88.8 | 77 | 68.9 |
| 9 | $K_{0.1}Ni_3Co_5Fe_2TeP_{0.5}Mo_{12}O_x$ | 91.9 | 73.2 | 76 | 55.3 |
| 10 | $Tl_{0.2}Ni_{2.5}Co_{4.5}Fe_3TeP_{0.5}Mo_{12}O_x$ | 88.5 | 87.5 | 71 | 62.0 |
| 11 | $In_{0.2}Ni_{2.5}Co_{4.5}Fe_3TeP_{0.5}Mo_{12}O_x$ | 88.9 | 79.2 | 79 | 62.2 |
| 12 | $K_{0.1}Ni_{2.5}Co_{4.5}Fe_3Sb_{0.5}Te_{0.5}P_{0.5}Mo_{12}O_x$ | 77.0 | 89.6 | 61 | 54.4 |

*Acrylonitrile
**Reaction run at 420° C.

Examples 13–16—Ammoxidation using catalysts containing optional components

In the same manner as described above, catalysts of the present invention containing various optional components were prepared and tested in the ammoxidation of propylene. After the heat treatment described in the examples above, the components of the catalysts in Examples 13–15 were heat treated at 650° C. for three hours. The catalyst in Example 16 was heat treated at 700° C. for two hours. The reactant ratios and contact times were the same as the examples above. The catalysts, reaction temperatures and results of the reactions are given in Table II.

TABLE II

AMMOXIDATION OF PROPYLENE USING CATALYSTS CONTAINING OPTIONAL COMPONENTS

| Example | Catalyst | Temp., °C. | % Conv. of Propylene | % Selectivity to AN* | % Per Pass Conv. to AN* |
|---|---|---|---|---|---|
| 13 | $Cr_{2.5}K_{0.1}Ni_{2.5}Co_{4.5}Fe_{0.5}TeP_{0.5}Mo_{12}O_x$ | 420 | 95.9 | 75 | 71.8 |
| 14 | $Ce_{1.5}K_{0.1}N_{2.5}Co_{4.5}Fe_{1.5}TeP_{0.5}Mo_{12}O_x$ | 420 | 71.9 | 73 | 52.6 |
| 15 | $Sb_{0.5}K_{0.1}Ni_{2.5}Co_{4.5}Fe_3Te_{0.5}P_{0.5}Mo_{12}O_x$ | 400 | 88.6 | 76 | 67.0 |
| 16 | $W_2K_{0.1}Ni_{2.5}Co_{4.5}Fe_3TeP_{0.5}Mo_{10}O_x$ | 420 | 75.2 | 86 | 64.5 |

*Acrylonitrile

Example 17—Ammoxidation Isobutylene

The catalyst prepared in Example 7 prior to heat treatment was heat treated at 650° C. for three hours. In the reaction of the examples above, a feed of isobutylene:$NH_3$:air:$H_2O$ of 1:1.1:10:4 was fed over the catalyst at a temperature of 420° C. and a contact time of six seconds. All of the isobutylene was reacted and the per pass conversion to methacrylonitrile was 57.1%.

In the same manner as described by the examples above, other catalysts of the invention, such as $CuNi_8Fe_2TeMo_{15}O_x$, $Zn_2MnMg_6FeTeMo_{12}O_x$, $Tl_{0.2}Ni_3Mg_4Fe_2TeP_{0.2}Mo_{12}O_x$, $Ag_{0.2}Rb_{0.1}Ni_3Co_6Fe_4Te_2B_{0.5}Mo_{1.6}O_x$, $Co_4Fe_{0.2}Te_3Mo_8O_x$, and $Ni_6Cd_2Fe_2TeMo_{12}O_x$ are prepared and employed in ammoxidation reactions.

We claim:

1. In the process for the preparation of acrylonitrile, methacrylonitrile or mixtures thereof by reacting propylene, isobutylene or mixture thereof with ammonia and molecular oxygen at a temperature between about 300° and about 600° C. in the presence of a catalyst, the improvement comprising: using as the catalyst an oxide catalyst having the formula:

$$A_aB_bC_cFe_dTe_fD_gMo_hO_x$$

wherein
A is an alkali metal, Tl, In, Cu, Ag or mixture thereof,
B is Ni, Co, Mg or mixtures thereof,
C is W, Cr, Ce, Zn, Cd, Mn, Cu, Ba or mixtures thereof,
D is P, As, Sb, B or mixture thereof,
and wherein
a and g are independently 0 to about 3,
b is about 6 to 8,
c is 0 to about 4,
d is about 0.1 to about 8,
f is about 0.04 to about 4,
h is 12,
x is the number of oxygens sufficient to satisfy the valence requirements of the other elements present,
and wherein b>d.

2. The process of claim 1 wherein B is Ni.
3. The process of claim 1 wherein B is Co.
4. The process of claim 1 wherein B is Ni and Co.
5. The process of claim 1 wherein A is an alkali metal, Tl, In or mixture thereof and a is not equal to zero.
6. The process of claim 1 wherein C is Cr, W or Ce and c is not equal to zero.
7. The process of claim 1 wherein D is P or Sb and g is not equal to zero.

* * * * *